US007281850B2

(12) United States Patent
Varadharajan et al.

(10) Patent No.: US 7,281,850 B2
(45) Date of Patent: Oct. 16, 2007

(54) METHOD AND APPARATUS FOR ALIGNING A FOURTH GENERATION COMPUTED TOMOGRAPHY SYSTEM

(75) Inventors: Sripriya Varadharajan, Fremont, CA (US); Souma Sengupta, Foster City, CA (US); Sanjay Kumar Jha, Foster City, CA (US); Brian Patrick Smyth, San Francisco, CA (US)

(73) Assignee: General Electric Company, Schenectady, NY (US)

(*) Notice: Subject to any disclaimer, the term of this patent is extended or adjusted under 35 U.S.C. 154(b) by 67 days.

(21) Appl. No.: 11/242,190

(22) Filed: Oct. 3, 2005

(65) Prior Publication Data

US 2007/0076841 A1   Apr. 5, 2007

(51) Int. Cl.
*G01D 18/00*   (2006.01)
(52) U.S. Cl. ............................ 378/207; 378/9; 378/10; 378/205
(58) Field of Classification Search ............... 378/9, 378/10, 15, 18, 20, 98.6, 205, 207, 7
See application file for complete search history.

(56) References Cited

U.S. PATENT DOCUMENTS

| 4,153,842 | A | * | 5/1979 | Rohmfeld | 378/9 |
|---|---|---|---|---|---|
| 4,190,773 | A | * | 2/1980 | Braden et al. | 378/10 |
| 4,203,036 | A | * | 5/1980 | Tschunt | 378/9 |
| 4,239,972 | A | * | 12/1980 | Wagner | 378/9 |
| 4,266,135 | A | * | 5/1981 | Kuwik et al. | 378/16 |
| 4,315,157 | A | * | 2/1982 | Barnes | 378/10 |
| 4,352,021 | A | * | 9/1982 | Boyd et al. | 378/12 |
| 4,392,235 | A | * | 7/1983 | Houston | 378/10 |
| 4,573,179 | A | * | 2/1986 | Rutt | 378/10 |
| 5,491,734 | A |   | 2/1996 | Boyd et al. | |
| 6,130,929 | A |   | 10/2000 | Saha | |
| 6,148,057 | A | * | 11/2000 | Urchuk et al. | 378/18 |
| 6,731,716 | B2 | * | 5/2004 | Mihara et al. | 378/9 |
| 6,789,943 | B2 | * | 9/2004 | Zapalac | 378/207 |
| 6,792,077 | B2 | * | 9/2004 | Rand | 378/149 |
| 7,016,456 | B2 | * | 3/2006 | Basu et al. | 378/18 |
| 7,103,233 | B2 | * | 9/2006 | Stearns | 382/289 |
| 2005/0047548 | A1 |   | 3/2005 | Sengupta et al. | |

* cited by examiner

*Primary Examiner*—Allen C. Ho
(74) *Attorney, Agent, or Firm*—Armstrong Teasdale LLP (57) ABSTRACT

A method and apparatus for the alignment of a fourth generation Computed Tomography (CT) system is provided. The method includes receiving X-ray scan data from the CT system, and processing the received X-ray scan data to automatically generate alignment correction information to align the CT system.

18 Claims, 9 Drawing Sheets

METHOD AND APPARATUS FOR ALIGNING A FOURTH GENERATION COMPUTED TOMOGRAPHY SYSTEM

BACKGROUND OF THE INVENTION

This invention relates generally to fourth generation computed tomography (CT) systems, and more particularly, to methods and apparatus for aligning fourth generation CT systems.

Electron Beam Computed Tomography (EBCT) or fourth generation Computed Tomography is a non-invasive imaging technique for acquiring images of human organs. To acquire images using a CT scanner, a source, for example, a focused electron beam is directed toward a target, for example, one or more tungsten targets. The focusing is typically performed using a set of coils. As the electron beam hits the tungsten targets, X-rays are produced. These X-rays are directed at a ring of detectors. In operation, the X-rays pass through the ring of collimators, the object that is to be imaged, and are then detected by the ring of detectors.

In a fourth generation CT system the tungsten targets, rings of collimators, and ring of detectors are positioned in different planes. Alignment between the ring of detectors, ring of collimators and the tungsten targets is needed as the position of the ring of detectors and the alignment of the ring of detectors with respect to the tungsten targets defines a cone angle of the CT scanner. If the ring of collimators, ring of detectors and the tungsten targets are not aligned, the cone angle will be different at different azimuthal angles. The difference in the cone angle may result in X-rays that originate at points diametrically opposite to each other not intersecting at the center of the scanner. If the X-rays that originate at points diametrically opposite to each other do not intersect at the center of the scanner, artifacts may be produced in an image.

Further, if the X-rays that originate at points diametrically opposite to each other do not intersect at the center of the scanner, the thickness of the object scanned in the z-direction in one scan cycle of the scanner, also called the slice profile, will vary non-uniformly from the isocenter of the scanner. In addition to the alignment, positioning of the detectors and the collimators in the z-direction relative to the targets is also needed. Non-alignment of the detectors in the z-direction relative to the targets causes the cone angle to be higher than the designed optimum cone angle for the CT system. Higher cone angle results in a greater amount of cone artifacts, for example, shading under the body parts to be scanned, such as ribs. These artifacts are difficult to correct during the reconstruction of an image.

Furthermore, any non-alignment of the ring of collimators and the ring of detectors can cause shading at the detectors. The result of the shading is that some of the X-ray dose that is given to the patient will not be detected, and therefore will not be used to generate an image.

In currently known methods for alignment of fourth generation CT systems, the process of alignment is performed manually using a cone phantom that is placed in the center of a scanner. The process is completely manual wherein an operator scans from a software service tool and then analyzes the data manually. The data analysis involves looking at sinograms and plots from the X-ray data generated from the scanning of the cone phantom, and making adjustments by moving the ring of collimators or the ring of detectors, for example, by using motors. The adjustment made by the operator is based on an estimate of the service engineer and are not predictive.

These known processes of alignment depend on the skill and the judgment of the operator and the service engineer. Thus, there is a higher likelihood of error, for example, because of user analysis, judgment and manual adjustment. Further, these processes are very time consuming.

BRIEF DESCRIPTION OF THE INVENTION

In an embodiment, a method for aligning a computed tomography (CT) system is provided. The method includes receiving X-ray scan data from the CT system and processing the received X-ray scan data to automatically generate alignment correction information to align the CT system.

In another embodiment, a computed tomography (CT) system is provided. The CT system includes a scanning portion for scanning an object to acquire X-ray scan data and a processing portion for processing the received X-ray scan data to automatically generate alignment correction information to align the CT system.

DETAILED DESCRIPTION OF THE INVENTION

Various embodiments of the present invention relate to a method for automatically generating alignment correction information to align a Computed Tomography (CT) system, and in particular, a fourth generation CT system. Cone plot analysis of scanner data is performed and used to adjust collimator motors or detector motors to align the CT system.

Figure 1:
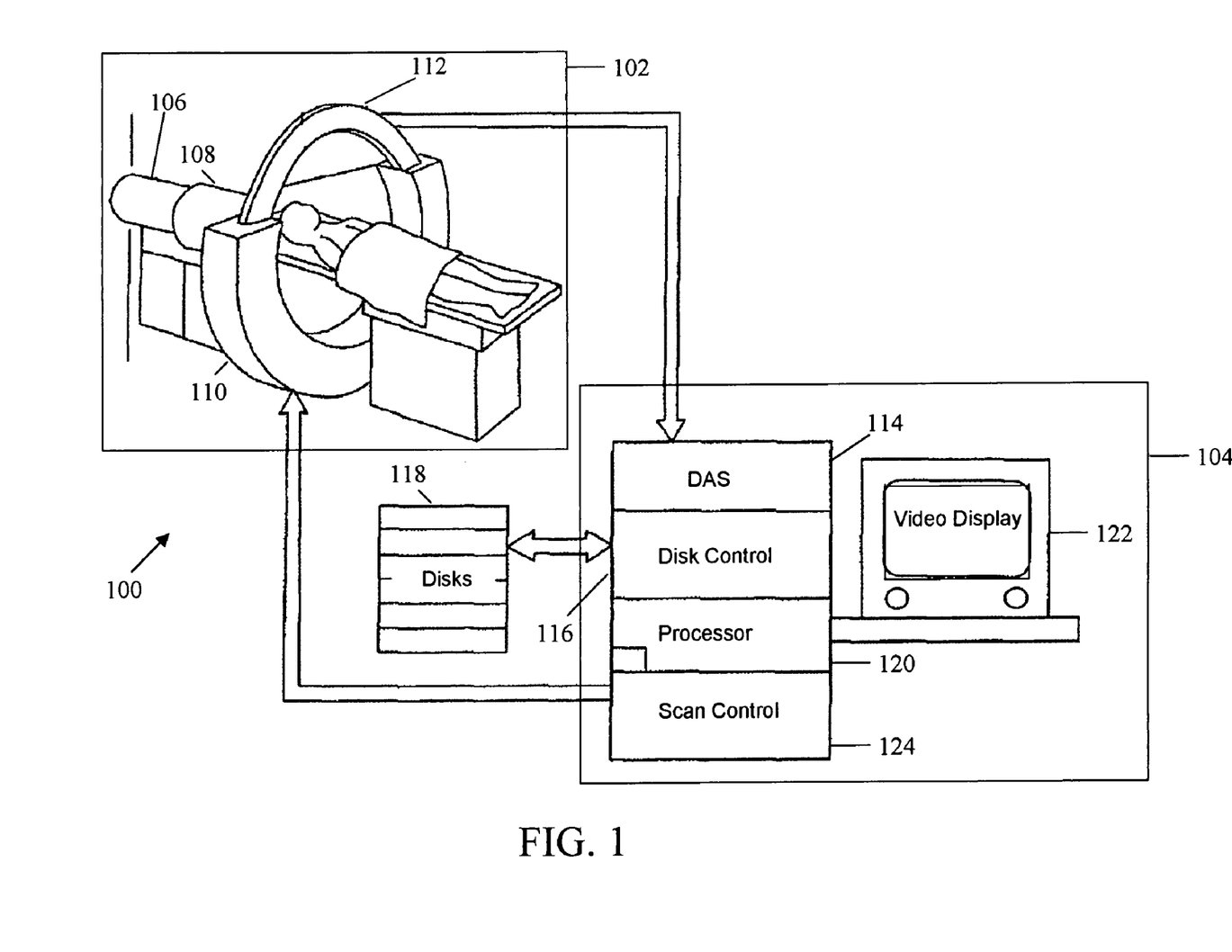
FIG. 1 is a diagram illustrating a fourth generation CT system in accordance with an embodiment of the invention.

FIG. 1 is a block diagram illustrating a fourth generation CT system 100 in accordance with an embodiment of the invention. CT system 100 includes a scanning portion 102 and a processing portion 104. Scanning portion 102 includes a source, for example, an electron source 106, electron focusing and deflection coils 108, gantry 110 and a ring of X-ray detectors 112. Electrons from electron source 106 pass through electron focusing and deflection coils 108 and impinge on tungsten targets (not shown). This causes generation of X-rays that pass through a ring of collimators in gantry 110, and are detected by ring of X-ray detectors 112.

Processing portion 104 includes Data Acquisition System (DAS) 114, disk control 116, disks 118, processor 120, video display 122, and scan control 124. Data generated when X-rays impinge on ring of X-ray detectors 112 are communicated to DAS 114. The data is collected by DAS 114 and controlled by disk control 116, provided (e.g., stored or written) to disks 118. Processor 120 accesses and obtains (e.g., reads) the data from disks 118 and reconstructs the data to form an image using 2D Fourier reconstruction. Video display 122 displays the image. In an embodiment of the invention, scan control 124 is used to control motors (not shown) that drive the ring of collimators and ring of X-ray detectors 112.

Figure 2:
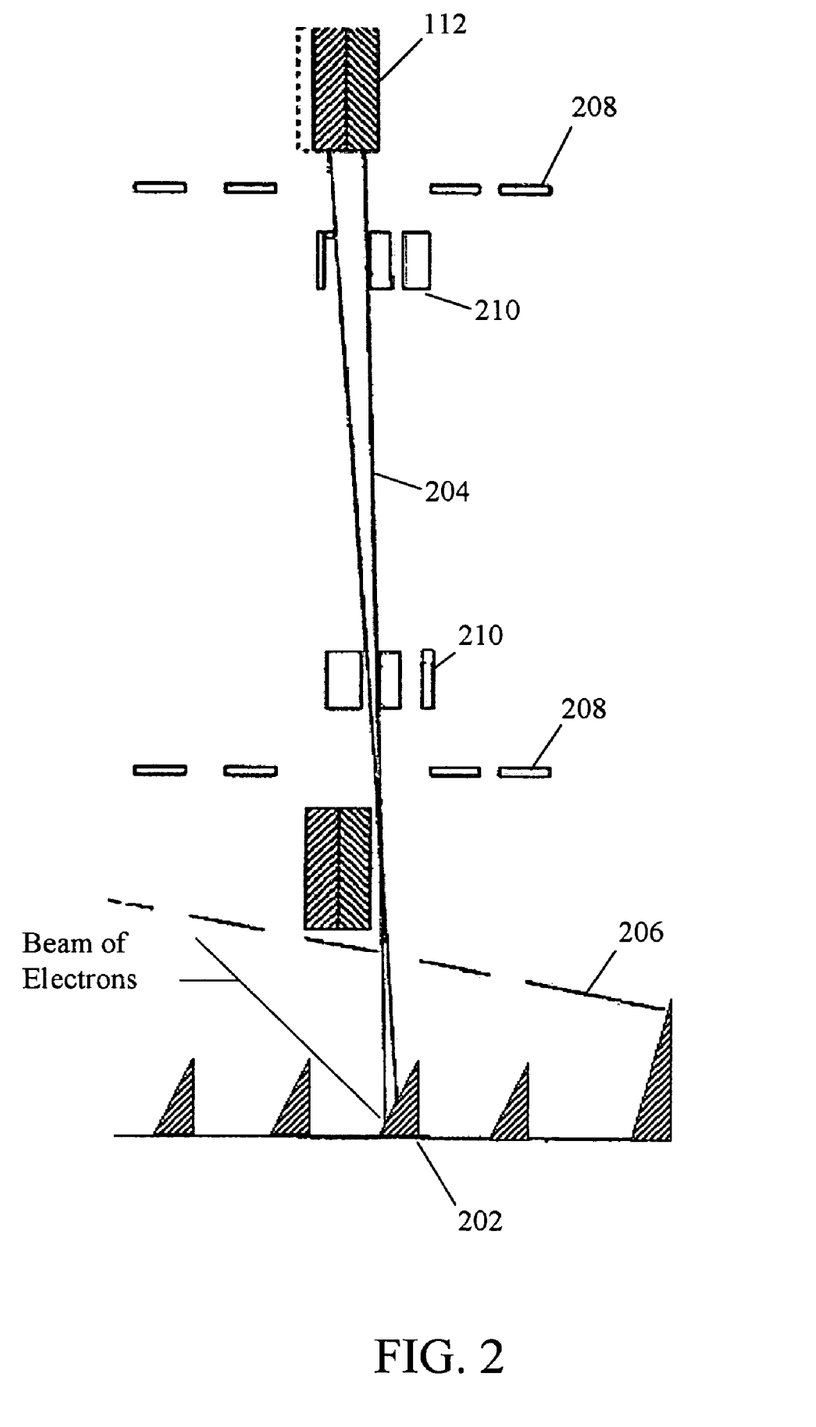
FIG. 2 is an illustration of a collimation system and a detector system in a fourth generation CT system in accordance with an embodiment of the invention.

FIG. 2 is an illustration of a collimation system and X-ray detectors 112 in CT system 100 in accordance with an embodiment of the invention. In an embodiment of the invention, an electron beam in the CT system 100 hits tungsten target 202 and generates an X-ray fan beam 204. In single slice mode of CT system 100, X-ray fan beam 204 passes through a ring of pre-collimators 206, a ring of brass collimators 208, and a ring of radiology collimators 210 before impinging on X-ray detectors 112.

In an exemplary mode of imaging using CT system 100, an object to be imaged is placed in the line of X-ray fan beam 204 inside ring of radiology collimators 210, in accordance with an embodiment of the invention. Artifacts may appear in the image of the object if tungsten target 202, ring of radiology collimators 210, and ring of X-ray detectors 112 are not aligned with respect to each other. In an embodiment of the invention, alignment between ring of radiology collimators 210 and ring of X-ray detectors 112 is achieved by performing a cone plot analysis. Cone plot analysis involves estimating points of intersection of a beam spot of X-ray fan beam 204 with a phantom placed in the center of scanning portion 102.

Figure 3:
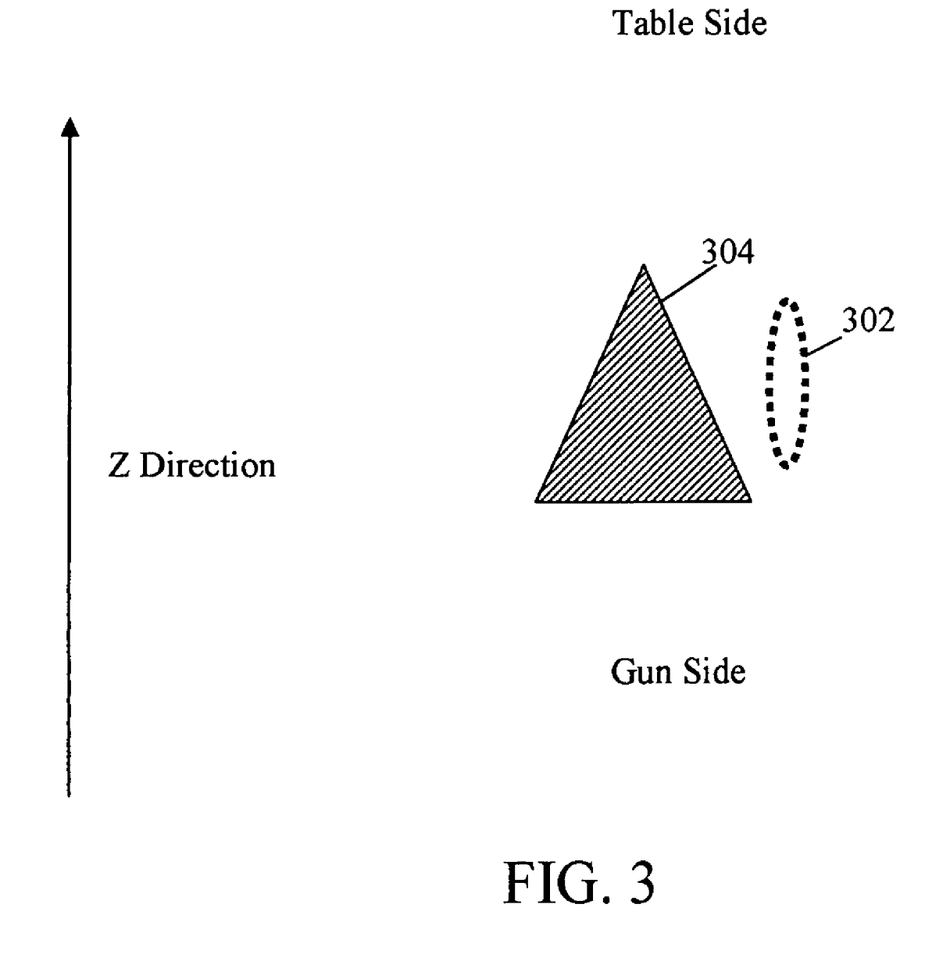
FIG. 3 is a diagram illustrating a beam spot that will be occluded by a phantom.
Figure 4:
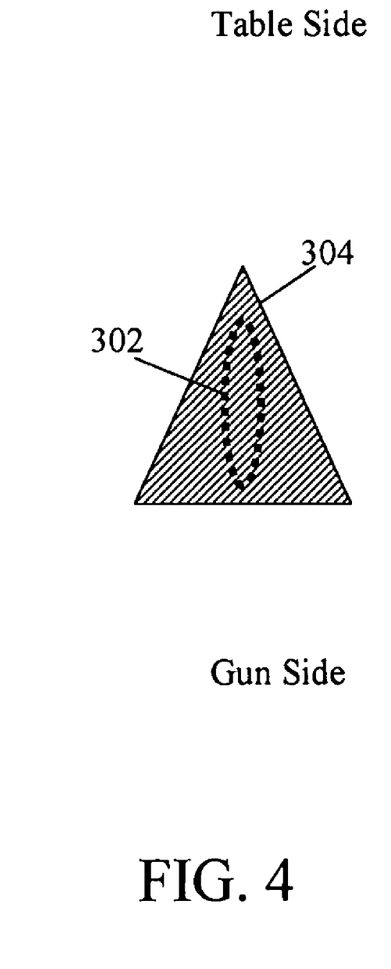
FIG. 4 is a diagram illustrating a beam spot being completely occluded by a phantom.

FIG. 3 and FIG. 4 illustrate a beam spot 302 of X-ray fan beam 204 (shown in FIG. 2) in relation to a phantom 304. FIG. 3 is a diagram illustrating a beam spot 302 that will be occluded by a phantom 304. FIG. 4 is a diagram illustrating beam spot 302 being completely occluded by phantom 304. In an embodiment of the invention, phantom 304 is a cone with a uniformly changing cross-section. Phantom 304 is mounted in the center of scanning portion 102 of CT system 100 such that the apex of phantom 304 is pointing away from electron source 106. Using this placement, the diameter of phantom 304 is wider towards the gun side than the table side of CT system 100. The gun side of CT system 100 is the side towards electron source 106. The table side of CT system 100 is the side away from electron source 106.

As X-ray fan beam 204 moves, the edge of beam spot 302 that is towards the gun side begins to be occluded by phantom 304. As X-ray fan beam 204 moves further, beam spot 302 is completely occluded as shown in FIG. 4. The same phenomenon occurs as beam spot 304 emerges on the table side of phantom 304. In an exemplary embodiment of the invention, beam spot 302 moves at a known velocity, and this velocity is used to calculate the diameter of phantom 304 at which the edge of X-ray fan beam 204 intercepts phantom 304. Knowing this diameter and the geometry of the cone, the distance of the intercept from the tip of the cone is computed. This distance is the intercept of X-ray fan beam 204 and phantom 304 in the axial or z-direction. There are two such intercepts, one with each edge of X-ray fan beam 204. These two intercepts are referred to as a gun side intercept and a table side intercept. These intercepts are calculated for each detector to get a pair of intercepts for different azimuthal angles. This pair of intercepts for each detector is used to construct a plot of the intercepts versus the detector. This plot of intercepts versus the detector is called a cone plot.

Various embodiments of using the X-ray scan data from phantom 304 to generate cone plots and perform cone plot analysis for generation of alignment correction information to align CT system 100 are explained in detail in conjunction with FIGS. 5 through 10.

Figure 5:
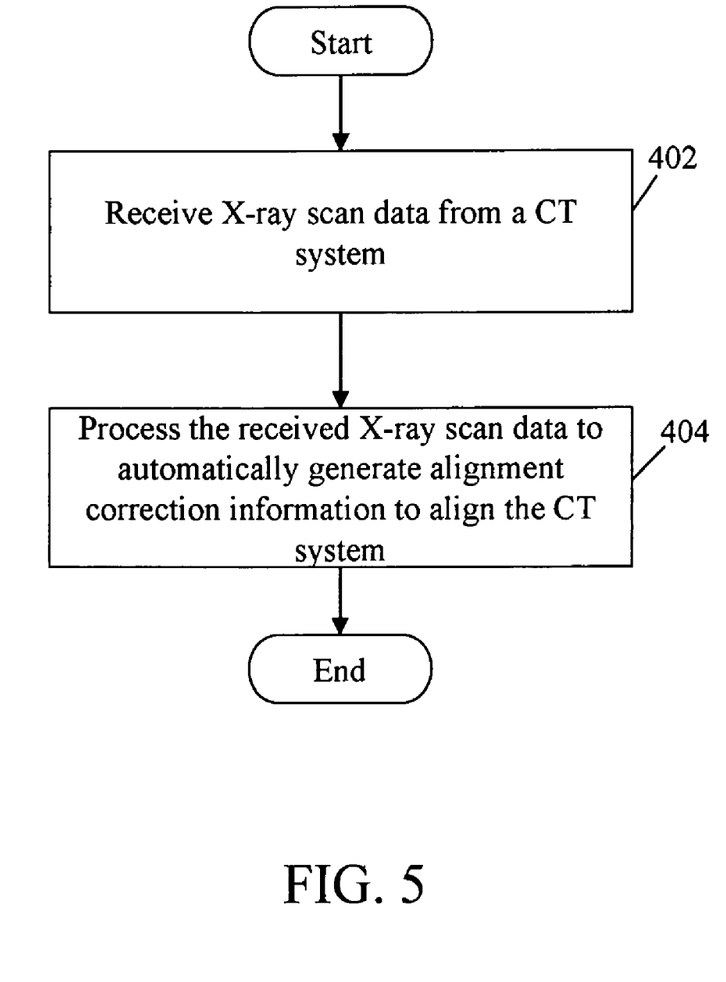
FIG. 5 is a flowchart illustrating a method of alignment of a CT system in accordance with an embodiment of the invention.

FIG. 5 is a flowchart illustrating a method of alignment of CT system 100 in accordance with an embodiment of the invention. At 402, X-ray scan data is received from CT system 100. At 404, the X-ray scan data is processed to automatically generate alignment correction information to align CT system 100.

More particularly, in an embodiment of the invention, the X-ray scan data received includes the X-ray scan data from the scanning of phantom 304. Gun side and table side cone plots are generated from the X-ray scan data of phantom 304. Gun side and table side cone plots are used to align CT system 100. The method of generating gun side and table side cone plots from X-ray scan data is explained in detail in conjunction with FIG. 6.

Figure 6:
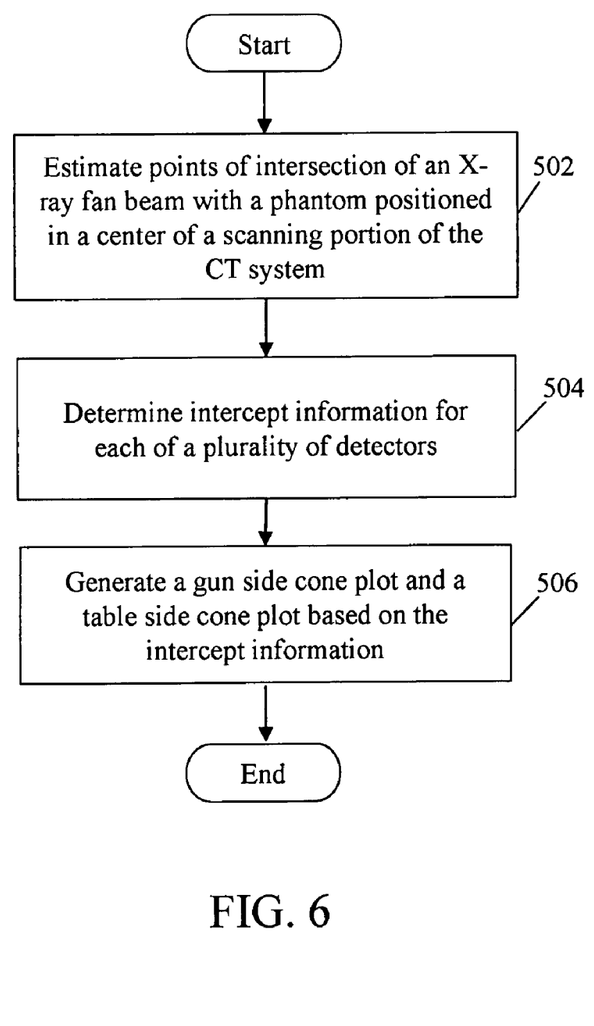
FIG. 6 is a flowchart illustrating a method of generating gun side and table side cone plots in accordance with an embodiment of the invention.

FIG. 6 is a flowchart illustrating a method for generating gun side and table side cone plots in accordance with an embodiment of the invention. At 502, points of intersection of beam spot 302 of X-ray fan beam 204 with phantom 304 are estimated. This computation is performed for both gun side and the table side based on normalized scan data. Points of intersection include points in time when each of the two edges of beam spot 302 moves behind and is occluded by phantom 304, and subsequently moves out from and is no longer occluded. As beam spot 302 and X-ray fan beam 204 move at a known velocity, and the geometry of phantom 304 is known, the above information is used to calculate the diameter of phantom 304.

At 504, the intercept of the two edges of the X-ray fan beam 204 and phantom 304 is determined for each detector in ring of X-ray detectors 112 (shown in FIG. 1). In an embodiment of the invention, the above intercept information for each X-ray detector includes the z-intercept information. The z-intercept information of X-ray fan beam 204 generated by beam spot 302 and phantom 304 is estimated using the x-ray data in a sinogram, the diameter of phantom 304, and the velocity of beam spot 302, along with the cone angle of CT system 100. The position of ring of X-ray detectors 112 (as shown in FIG. 1), and alignment of ring of X-ray detectors 112 with respect to tungsten target 202 defines the cone angle of CT system 100.

In an embodiment of the invention, normalized sinograms are used to calculate the z-location of edge intercepts of X-ray fan beam 204 with phantom 304. Normalized sinograms are the data sinograms divided by the air (i.e., with nothing in the center of scanning portion 102).

The intercepts referred to above are the intercept of the edge of X-ray fan beam 204 with phantom 304. X-ray fan beam 204 has two such intercepts in z direction, the gun side and the table side. At 506, gun side and table side cone plots are generated using the intercept information. The cone plots are generated using the intercept information for each X-ray detector in ring of X-ray detectors 112 for the gun side and table side, the average of the gun side and table side intercept information for each X-ray detector, and the difference between the gun side and table side intercept information for each X-ray detector.

When ring of X-ray detectors 112 is aligned with respect to ring of collimators 210, a cone plot generated is flat and smooth. If the cone plot is not flat, then ring of X-ray detectors 112, ring of radiology collimators 210 must be aligned with respect to each other. In an embodiment of the invention, alignment is performed by estimating the amount of tilting and slewing to be provided at ring of radiology collimators 210 by using the alignment correction information generated using the cone plots. Ring of radiology collimators 210 is then adjusted until the cone plots are flat. A method of calculating the amount of tilting and slewing to be provided is explained in conjunction with FIG. 7, FIG. 8, and FIG. 9.

Figure 7:
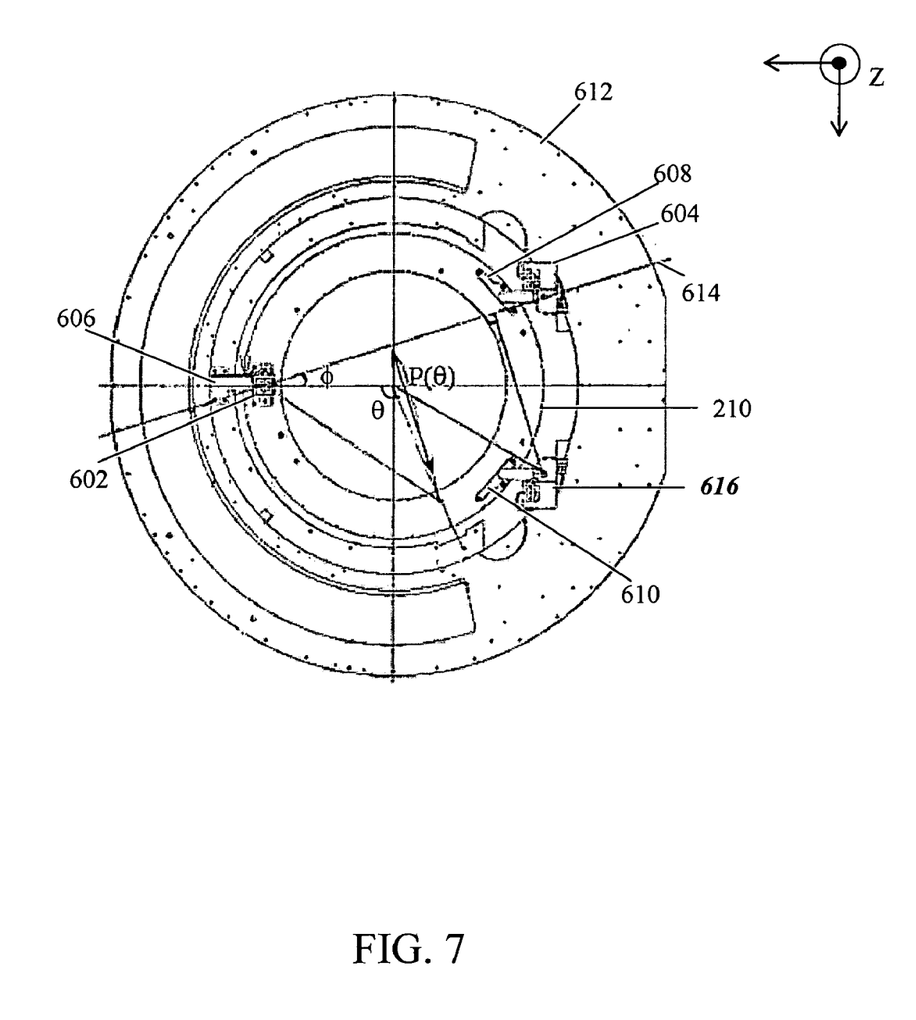
FIG. 7 is a diagram illustrating the geometry of a ring of radiology collimators of a fourth generation CT system for calculating alignment correction information for two motors in accordance with an embodiment of the invention.

FIG. 7 is a diagram illustrating the geometry of ring of radiology collimators 210 of CT system 100 for calculating alignment correction information for motor 616, in accordance with an embodiment of the invention. Ring of radiology collimators 210 is mounted at three points, mounting point 606, mounting point 608, and mounting point 610 on main flange 612 of CT system 100. All degrees of freedom of movement of ring of radiology collimators 210 are about these three mounting points. Motor 602 moves mounting point 606, motor 604 moves mounting point 608, and motor 616 moves mounting point 610. The axis of movement of ring of radiology collimators is 614 when motor 616 is moved. Motor 602 and motor 604 are controlled, for example, by a computer, in accordance with an embodiment of the invention.

Figure 8:
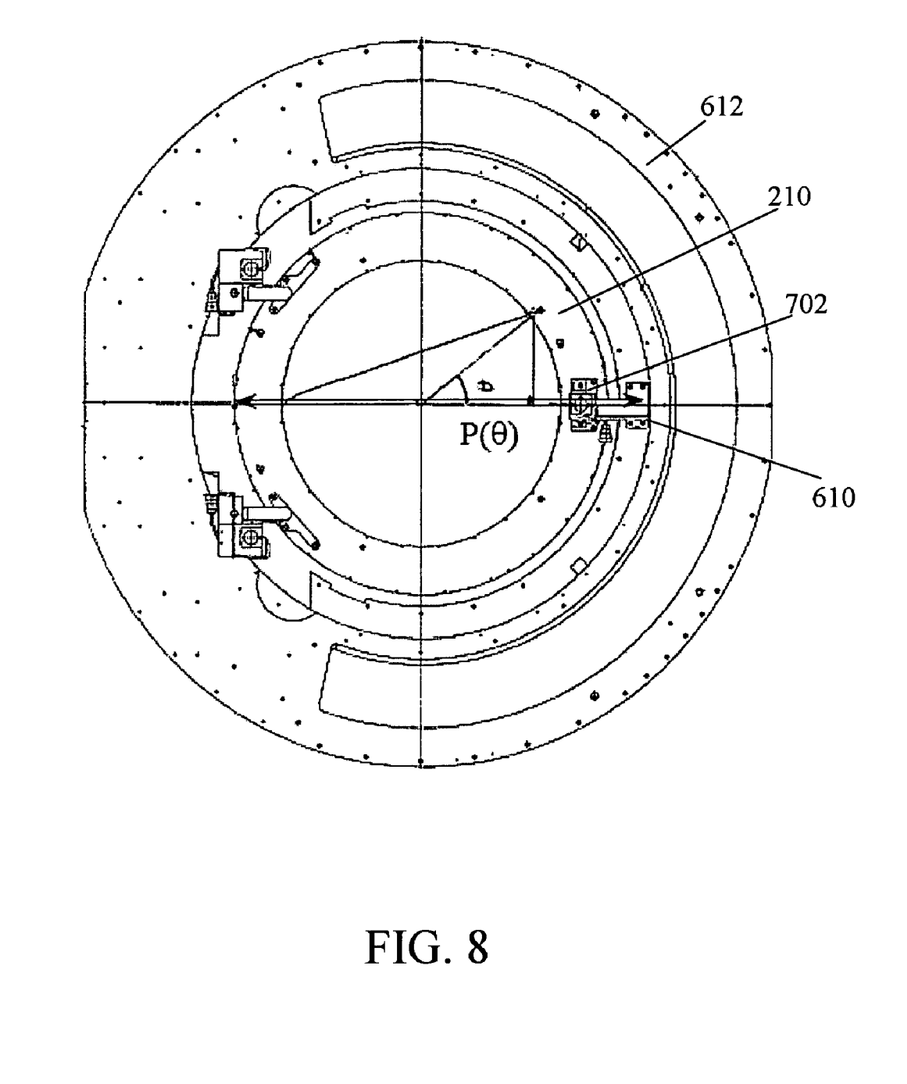
FIG. 8 is an alternative diagram illustrating the geometry of a ring of radiology collimators of a fourth generation CT system for calculating alignment correction information for a third motor in accordance with an embodiment of the invention.

FIG. 8 is an alternative diagram illustrating the geometry of ring of radiology collimators 210 of CT system 100 for calculating alignment correction information for motor 702, in accordance with an alternative embodiment of the invention. FIG. 8 illustrates several elements that are the same or similar to corresponding elements illustrated in FIG. 7. Accordingly, these elements are referenced in FIG. 8 using the same element reference numerals used in FIG. 7. Motor 702 controls movement of mounting point 610. Motor 702 is controlled by, for example, a computer, in accordance with an embodiment of the invention.

Figure 9:
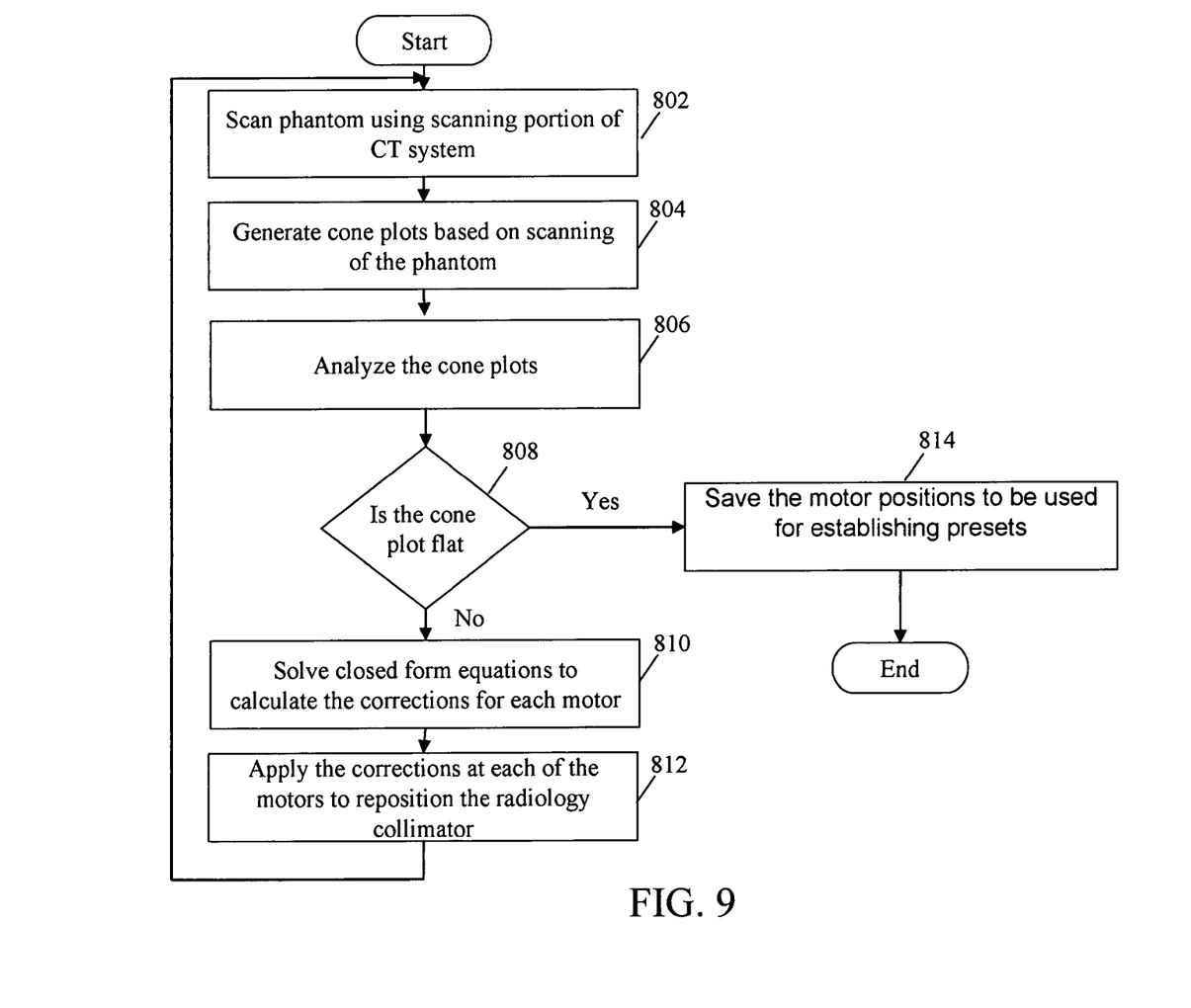
FIG. 9 is a flowchart illustrating a method for generating alignment correction information to align a CT system in accordance with an embodiment of the invention.

FIG. 9 is a flowchart of a method for generating alignment correction information to align CT system 100 in accordance with an embodiment of the invention. This alignment correction information is then used to align ring of radiology collimators 210 with respect to ring of X-ray detectors 112, and thereby produce uniform size slices, and reduce or eliminate shading of X-rays at the detectors in ring of X-ray detectors 112.

At 802, phantom 304 (shown in FIGS. 3 and 4) is scanned using scanning portion 102 (shown in FIG. 1). At 804 cone plots are generated using X-ray scanning data of phantom 304.

At 806, the cone plots generated are analyzed. The cone plots are analyzed by measuring the deviation of the cone plot from a flat line for all azimuthal angles. These deviations are the errors from the nominal cone plot. At 808, if the cone plots are not flat, ring of radiology collimators 210 is aligned with ring of X-ray detectors 112 to make the cone plots flat. The process of alignment involves minimizing the sum of errors by using motor 602, motor 604 and motor 702 to move mounting point 606, mounting point 608, and mounting point 610.

At 810, closed form equations are solved to calculate corrections for motor 602, motor 604, and motor 702. Correction for motor 602 and motor 604 is calculated using the geometry as shown in FIG. 7.

For illustrative purposes, the azimuthal angles of motor 602 is $\theta_{m1}=-150°$, motor 702 is $\theta_{m2}=-0°$, and motor 604 is $\theta_{m3}=150°$.

For calculating the error in alignment due to motor 604, the perpendicular distance of a point to axis of rotation 614 is $P(\theta)$, where $P(\theta)$ is calculated by the following Equation 1:

$$P(\theta)=2*r_c*\sin|\theta/2|*\sin(90-|\theta/2|+\phi) \qquad (1)$$

Where $\theta$ is the azimuthal angle, and $\phi$ is $-20°$ (FIG. 7, measured to be $-20°$ For error $\Delta Z_1(\theta)$ due to misalignment of motor 602, the following Equation 2 is used:

$$\Delta Z_1(\theta)=P(\theta)/P(150)*\Delta Z_{m1} \text{ where } \Delta Z_{m1} \text{ is the positioning error at motor 602} \qquad (2)$$

Motion at the collimating edge i.e., inside edge of the collimator $\Delta Z_{1, coll}$ is calculated by the following Equation 3:

$$\Delta Z_{1, coll}(\theta)=r_c/r_{m1}*\Delta Z_1(\theta)=[1/P(150)]*[r_c/r_{m1}]$$
$$*2*r_c*\sin|\theta/2|*[\sin(90-|\theta/2|+\phi)]*\Delta Z_{m1} \qquad (3)$$

Where $r_{m1}$, $r_{m2}$, $r_{m3}$ are radii of motor 602, motor 702, and motor 604 respectively, and $r_c$ is radius of inside (collimating) edge of the radiology collimator.

At the center of scanning portion 102, the cone intercept is calculated by the following Equation 4 or 5:

$$\Delta Z_{1, cone}(\theta)=r_t/(r_t-r_c)*\Delta Z_{coll}(\theta)*\text{sign} \qquad (4)$$

$$\Delta Z_{1, cone}(\theta)=r_t/(r_t-r_c)*1/P(150)*r_c/r_{m1}*2*r_c*\sin|\theta/2|*\sin(90-|\theta/2|+\phi) \text{ sign}*\Delta Z_{m1} \qquad (5)$$

Where sign=$-1$ for $-150<\theta<0$ and sign=$1$ for $0<\theta<150$, and $r_1$ radius of the target. In an embodiment of the invention, this can be represented by the following Equation 6:

$$\Delta Z_{1, cone}(\theta)=f_1(\theta)*\Delta Z_{m1} \qquad (6)$$

For calculating the error ($\Delta Z_2(\theta)$) in alignment due to motor 702 (FIG. 8) the following Equation 7 is used:

$$\Delta Z_{2, cone}(\theta)=[r_t/(r_t-r_{tc})]*[(r_c \cos \theta+d)/(r_c+d)]*\Delta Z_{m2} \qquad (7)$$

Where $\Delta Z_{m2}$ is the positioning error at motor 702, d=$r_c \cos \phi$=15 degrees This can be represented by:

$$\Delta Z_{2, cone}(\theta)*\Delta Z_{m2} \qquad (8)$$

For calculating the error ($\Delta Z_3(\theta)$) in alignment due to motor 616 the following Equation 9 is used:

$$\Delta Z_{3, cone}(\theta)=[r_t/(r_t-r_{tc})]*[1/P(150)]*[r_c/r_{m1}]$$
$$*2*r_c*\sin|\theta/2|*\sin(90-|\theta/2|-\phi)*\text{sign}*\Delta Z_{m3} \qquad (9)$$

Where sine=1 for $-150°<\theta<0°$ and sine=$-1$ for $0°<\theta<150°$

This can be represented by:

$$\Delta Z_{3, cone}(\theta)=f_3(\theta)*\Delta Z_{m3} \qquad (10)$$

The total error $\Delta Z_{total}(\theta)$ is calculated by the following Equation 11:

$$\Delta Z_{total}(\theta)=f_1(\theta)*\Delta Z_{m1}+f_2(\theta)*\Delta Z_{m2}+f_3(\theta)*\Delta Z_{m3} \qquad (11)$$

In an embodiment of the invention, in order to minimize the sum of squares error F is minimized where F is represented by the following Equation 12:

$$F = \sum_{\Theta=-150}^{\Theta=150} \left( \frac{\Delta Z_{measured}(\theta) - f_1(\theta) * \Delta Z_{m1} + f_2(\theta) *}{\Delta Z_{m2} + f_3(\theta) * \Delta Z_{m3}} \right)^2 \quad (12)$$

Taking partial derivatives with respect to the three motors and equating to 0 the following equations are generated:

$$\partial F / \partial M_1 = 0 \quad (13)$$

$$\partial F / \partial M_2 = 0 \quad (14)$$

$$\partial F / \partial M_3 = 0 \quad (15)$$

In an embodiment of the invention, these equations are represented as:

$$\frac{\partial F}{\partial M_1} = \sum_{\theta=-150}^{\theta=150} f_1, \theta Z_{measured}(\theta_i) - \Delta Z_{m1} \sum_{\theta=-150}^{\theta=150} f_1^2, \theta - \Delta Z_{m2} \sum_{\theta=-150}^{\theta=150} f_1, \theta f_2, \theta - \Delta Z_{m3} \sum_{\theta=-150}^{\theta=150} f_1, \theta f_3, \theta = 0 \quad (16)$$

$$\frac{\partial F}{\partial M_2} = \sum_{\theta=-150}^{\theta=150} f_2, \theta Z_{measured}(\theta_i) - \Delta Z_{m1} \sum_{\theta=-150}^{\theta=150} f_1, \theta f_2, \theta - \Delta Z_{m2} \sum_{\theta=-150}^{\theta=150} f_2^2, \theta - \Delta Z_{m3} \sum_{\theta=-150}^{\theta=150} f_2, \theta f_3, \theta = 0 \quad (17)$$

$$\frac{\partial F}{\partial M_3} = \sum_{\theta=-150}^{\theta=150} f_{3,i}, \theta Z_{measured}(\theta_i) - \Delta Z_{m1} \sum_{\theta=-150}^{\theta=150} f_1, \theta f_3, \theta - \Delta Z_{m2} \sum_{\theta=-150}^{\theta=150} f_2, \theta f_\theta^2 - \Delta Z_{m3} \sum_{\theta=-150}^{\theta=150} f_{3,\theta}^2 = 0 \quad (18)$$

In an embodiment of the invention the above equations are written as:

$$\begin{bmatrix} C_{11} & C_{12} & C_{13} \\ C_{21} & C_{22} & C_{23} \\ C_{31} & C_{32} & C_{33} \end{bmatrix} \times \begin{bmatrix} \Delta Z_{m1} \\ \Delta Z_{m2} \\ \Delta Z_{m3} \end{bmatrix} = \begin{bmatrix} R_1 \\ R_2 \\ R_c \end{bmatrix} \quad (19)$$

$$C_{11} = \sum_{\theta=-150}^{\theta=150} f_{1,\theta}^2, C_{12} \quad (20)$$

$$= \sum_{\theta=-150}^{\theta=150} f_1, \theta f_2, \theta, C_{13}$$

$$= \sum_{\theta=-150}^{\theta=150} f_1, \theta f_3, \theta$$

$$= 0, R_1$$

$$= \sum_{\theta=-150}^{\theta=150} f_1, \theta Z_{measured}(\theta i)$$

$$C_{21} = \sum_{\theta=-150}^{\theta=150} f_1, \theta f_2, \theta, C_{22} \quad (21)$$

$$= \sum_{\theta=-150}^{\theta=150} f_{2,\theta}^2, C_{23}$$

$$= \sum_{\theta=-150}^{\theta=150} f_2, \theta f_3, \theta = 0, R_2$$

$$= \sum_{\theta=-150}^{\theta=150} f_2, \theta Z_{measured}(\theta i)$$

$$C_{31} = \sum_{\theta=-150}^{\theta=150} f_1, \theta f^3 \theta, C_{32} \quad (22)$$

$$= \sum_{\theta=-150}^{\theta=150} f_{2,\theta} f_\theta^2, C_{33}$$

$$= \sum_{\theta=-150}^{\theta=150} f_{3,\theta}^2$$

$$= 0, R_3$$

$$= \sum_{\theta=-150}^{\theta=150} f_{3,i} Z_{measured}(\theta i)$$

Equations 20, 21, and 22 are solved to calculate the corrections required to align ring of radiology collimators 210 at motor 602 ($\Delta Z_{m1}$), at motor 702 ($\Delta Z_{m2}$) and at the motor 604 ($\Delta Z_{m3}$).

The amount of correction at each mount is calculated based on the above method. These corrections are applied to the respective motors 812, phantom 304 is scanned, and the errors are computed again.

At 808, iterative processing is continued until the cone plot is flat or within a predetermined range. Adjustments in the alignment are made at the mounting points such that the combination of three adjustments results in a least-squares-error sum from the "flat" cone plot. In an ideally aligned scanner both gun side and table side cone plots should be a straight line of a constant magnitude (i.e. parallel to the abscissa). This is referred to as flat cone plot. At this point, the slice width should also be uniform.

At 808, if the criterion of flatness of cone plots is met, the positions of motors are saved for establishing presets 814.

Figure 10:
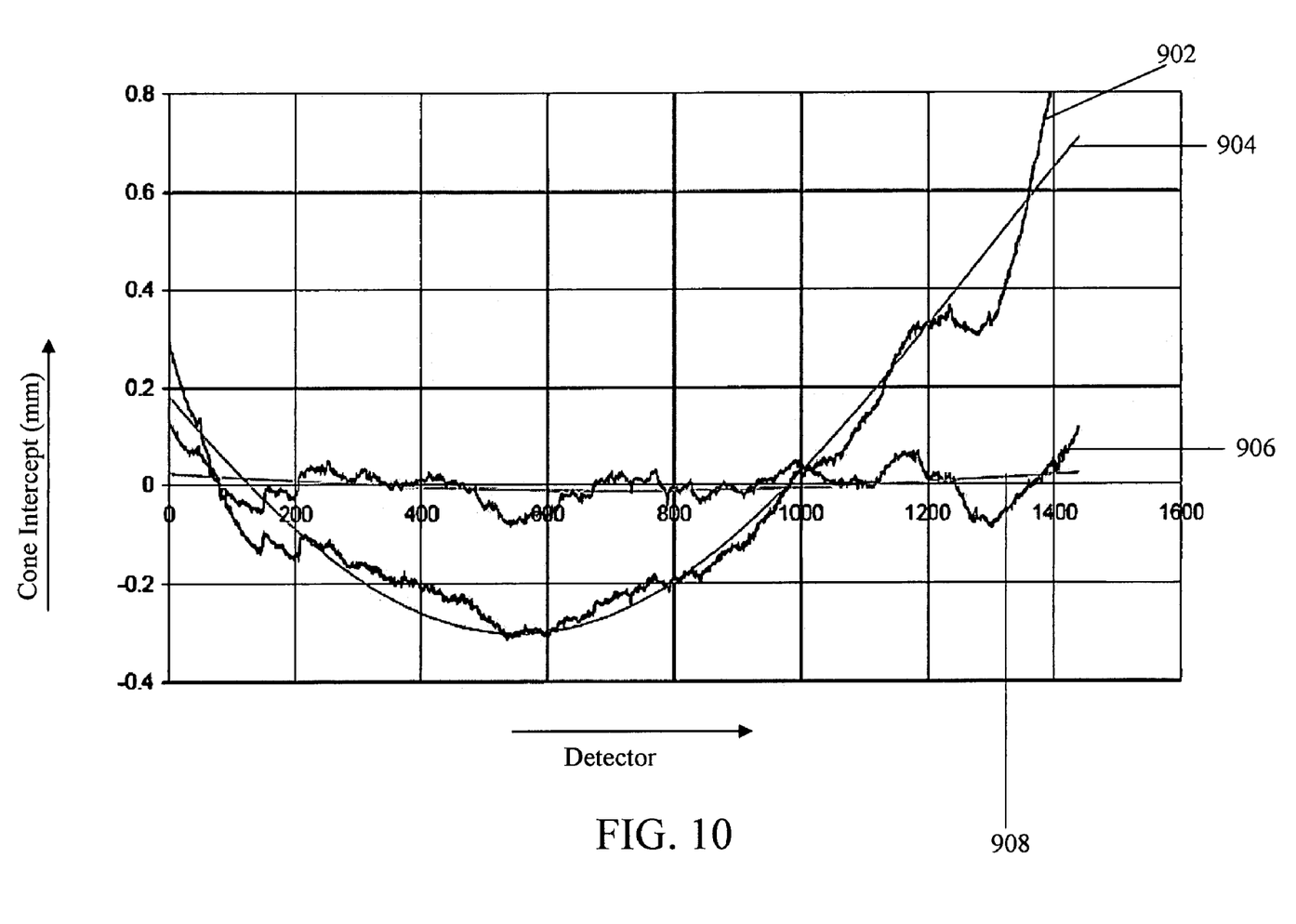
FIG. 10 is a graph illustrating the results of auto-flattening of cone plots in accordance with an embodiment of the invention.

FIG. 10 is an illustration of the results of auto-flattening of the cone plots in accordance with an embodiment of the invention where 902 represents the start of alignment, 906 represents the end alignment, 904 represents the best-fit at the starting position, and 908 represents the best-fit at the end of the alignment. At the end of the alignment, the detector ring and the radiology collimator are parallel to each other and are nominally in a plane perpendicular to the z-axis of CT system 100. Also, at these positions of ring of X-ray detectors 112 and ring of radiology collimators 210 there is minimal or no shading of the image. A well aligned scanner involves ensuring that no part of the detector-view sinogram is shaded, and the cone plot is flat, as indicated at 908.

Various embodiments of the invention provide methods that result in repeatable and reliable alignment of the CT system. This results in predictable and uniform repeatable image quality across all CT systems. The various embodiments automate the alignment process such that operator intervention is minimized. Operator intervention is needed to place phantoms and move objects, for example, mounts and screws by amounts that are calculated using the various embodiments of the invention. No trial and error steps where objects are moved by estimates of the operator are used.

Moreover, the various embodiments of the invention also provide for aligning CT systems iteratively until a predetermined specification of flatness is met, resulting in predictable image quality.

Various embodiments of the invention are not limited to CT systems with a fourth generation geometry, but can be implemented in connection with different CT systems.

While the invention has been described in terms of various specific embodiments, those skilled in the art will recognize that the various embodiments of the invention can be practiced with modification within the spirit and scope of the claims.

What is claimed is:

1. A method for aligning a computed tomography (CT) system, the method comprising:
   receiving X-ray scan data from the CT system;
   processing the received X-ray scan data to automatically generate alignment correction information to align the CT system; and
   aligning a detector ring including a plurality of detectors and a collimator ring of the CT system based on the alignment correction information.

2. A method in accordance with claim 1 further comprising scanning a phantom to acquire the X-ray scan data.

3. A method in accordance with claim 2 wherein the phantom comprises an object having a uniformly changing cross-section.

4. A method in accordance with claim 1 further comprising scanning a phantom positioned in the CT system to facilitate determining from the received X-ray scan data intercept information for each of a plurality of detectors of the CT system.

5. A method in accordance with claim 4 further comprising generating a cone plot based on the intercept information.

6. A method in accordance with claim 5 further comprising iteratively processing the received X-ray scan data to generate a flat cone plot.

7. A method in accordance with claim 5 further comprising iteratively processing the received X-ray scan data to generate a cone plot such that a crystal array of a detector array of the CT system is uniformly in a plane perpendicular to a z-axis of a scanning portion of the CT system.

8. A method in accordance with claim 4 wherein the intercept information comprises z-intercept information.

9. A method in accordance with claim 4 wherein determining the intercept information comprises calculating intercepts based on generated sinograms.

10. A method in accordance with claim 4 further comprising generating a gun side cone plot and a table side cone plot based on the intercept information.

11. A method in accordance with claim 4 wherein determining the intercept information comprises determining when an X-ray beam is obstructed by a phantom being scanned.

12. A method in accordance with claim 1 wherein the CT system comprises a fourth-generation CT scanner.

13. A method in accordance with claim 1 wherein the processing comprises estimating points of intersection of an X-ray fan beam with a phantom positioned in a center of a scanning portion of the CT system.

14. A method in accordance with claim 1 wherein the processing comprises calculating from normalized sinograms a z-location of edge intercepts of an X-ray fan beam with a phantom.

15. A method for aligning a computed tomography (CT) system, the method comprising:
   scanning a phantom using a scanning portion of the CT system;
   generating a cone plot based on the scanning of the phantom;
   iteratively processing the cone plot to automatically generate alignment correction information to align the CT system, the iterative processing including iteratively generating cone plots after each of an adjustment to the scanning portion of the CT system with the iterative processing continuing until the cone plot is flat; and
   aligning a detector ring including a plurality of detectors and a collimator ring of the CT system based on the alignment correction information.

16. A method in accordance with claim 15 further comprising determining intercepts of an X-ray beam with the phantom based on when the X-ray beam is obstructed by the phantom, the intercepts used to generate the cone plot.

17. A computed tomography (CT) system comprising:
   a detector ring including a plurality of detectors;
   a collimator ring;
   a scanning portion that scans an object to acquire X-ray scan data; and
   a processing portion that processes the X-ray scan data to automatically generate alignment correction information to align the CT system, said detector ring and said collimator ring aligned based on the alignment correction information.

18. A CT system in accordance with claim 17 wherein the processing portion is further configured to determine from the received X-ray scan data intercept information for each of a plurality of detectors of the scanning portion and to generate a cone plot based on the intercept information, wherein the received X-ray scan data is iteratively processed to generate a flat cone plot.

* * * * *